(12) United States Patent
Webster

(10) Patent No.: US 6,610,762 B1
(45) Date of Patent: Aug. 26, 2003

(54) ADHESIVES

(75) Inventor: Iain Webster, Wilberfoss (GB)

(73) Assignee: Smith & Nephew Plc, London (GB)

( * ) Notice: Subject to any disclaimer, the term of this patent is extended or adjusted under 35 U.S.C. 154(b) by 0 days.

(21) Appl. No.: 09/509,577

(22) PCT Filed: Oct. 2, 1998

(86) PCT No.: PCT/GB98/02973

§ 371 (c)(1),
(2), (4) Date: May 9, 2000

(87) PCT Pub. No.: WO99/18136

PCT Pub. Date: Apr. 15, 1999

(30) Foreign Application Priority Data

Oct. 2, 1997 (GB) ................................................ 9720922

(51) Int. Cl.⁷ .................................................. C08F 2/46
(52) U.S. Cl. ...................... 522/120; 522/113; 522/114; 522/116; 522/119; 522/121; 522/126; 522/149; 522/150; 522/154; 522/134; 522/135; 522/141; 428/345; 428/343; 428/355 R; 428/355 AC; 156/272.2
(58) Field of Search ........................... 523/111; 522/90, 522/96, 134, 135, 113, 114, 116, 120, 126, 136, 141, 144, 119, 149, 150, 153; 156/272.2; 428/345, 343, 355 AC, 355 R

(56) References Cited

U.S. PATENT DOCUMENTS

| 2,973,286 | A | * | 2/1961 | Ulrich et al. | ................. | 117/122 |
| 4,762,888 | A | * | 8/1988 | Sun et al. | .................... | 525/125 |
| 4,879,178 | A | * | 11/1989 | Sun et al. | .................... | 428/355 |
| 5,433,892 | A | * | 7/1995 | Czech | ........................ | 252/500 |

FOREIGN PATENT DOCUMENTS

WO 97/06836 * 2/1997

* cited by examiner

Primary Examiner—James J. Seidleck
Assistant Examiner—Sanza L. McClendon
(74) Attorney, Agent, or Firm—Larson & Taylor PLC

(57) ABSTRACT

An adhesive composition which is switchable under irradiation to change from a tacky to a less tacky state which includes a switchable polymer. The polymer comprises a backbone polymeric moiety bound to a plurality of curable moieties, each of which comprises a free-radically active group and has an amine functionality. Also, the switchable polymer, processes for producing such polymers and compositions, and switchable adhesive articles comprising the adhesive compositions, such as light-switchable pressure sensitive adhesive dressings, and methods of using such articles.

9 Claims, 1 Drawing Sheet

ADHESIVES

The present invention relates to adhesive compositions, and to processes for producing adhesive compositions. It also relates to polymers for use in such compositions, and to processes for producing such polymers. It further relates to articles comprising adhesive compositions and to methods of using such articles. In particular this invention relates to 'switchable' adhesive compositions, that is, adhesive compositions capable of being influenced to change from a tacky to a less tacky, or even non-tacky, state thereby reducing the peel strength of the adhesive composition.

Adhesive products such as adhesive surgical or medical dressings and bandages normally comprise a layer of a pressure sensitive adhesive. However, when conventional adhesive dressings and/or bandages are removed, they often cause localised trauma to the patient.

There has therefore long been a desire to provide adhesive dressings that can exhibit a reduction in peel strength of the adhesive, for example by being capable of being changed from a tacky to a less tacky, or even non-tacky, state. Such 'switchable adhesives' would cause less localised trauma than conventional adhesives when the dressing is removed.

Switchable adhesives are known. For example, U.S. Pat. Nos. 5,032,637, 5,352,516, 4,331,576 and 5,182,323 describe adhesives that become less tacky, that is, are switchable, in contact with water. However, such adhesives are unsuitable, for example, if used on a wound dressing and the patient's wound needs to be kept dry. UV switchable adhesives are described in U.S. Pat. Nos. 4,286,047, 4,968,559 and 5,118,567 and Japanese Patent No.3043988. Such adhesives suffer from the disadvantage that they may require high doses of UV radiation or may need to be used in conjunction with photoinitiators which result in undesirable by-products. It remains undesirable to expose patients to too much ultra violet radiation.

There therefore remains a need for a switchable adhesive that can undergo a reduction in peel strength at low dosages of UV radiation or more preferably by exposure to visible light irradiation.

In our International Patent Publication No WO 97/06836 we describe a switchable adhesive formulation. This comprised inter alia a modified acrylic adhesive based on copolymers of alkyl acrylates, acrylic acid and/or a free radical polymerisable vinyl moiety, functionalised by a curable moiety bonded thereto. Such curable moieties include those derived from anthracenes, cinnamates, maleimides, coumarins, acrylates and/or methacrylates.

One problem associated with the use of such moieties is the difficulty in synthesis and their relatively aggressive adhesive characteristics. The polymerisation of some preferred prior art and even subsequent methacrylate functionalised switchable adhesives requires the use of multiple solvents in order a) firstly to produce a polymer having a sufficiently high molecular weight for it to be used as a medical adhesive and b) secondly to carry out the reaction of the functionalising moiety with the main polymer chain.

We have now surprisingly found an adhesive that is switchable when exposed to radiation, in particular to electromagnetic, especially actinic radiation, that is, visible or UV light. Such switchable adhesive has better adhesive properties than known switchable adhesives and is novel.

Thus according to one feature of the present invention we provide a switchable adhesive composition capable of being influenced by radiation to change from a tacky to a less tacky state which includes a switchable polymer comprising a backbone polymeric moiety having a plurality of curable moieties bonded thereto, characterised in that at least a proportion of the curable moieties each comprises a free-radically active group and has an amine functionality.

When used herein, the term 'free-radically active group' means any group that can undergo addition to another group by free radical transfer.

When used herein, the term 'amine functionality' includes amino functions further functionalised by other groups, for example in particular, amido functions and substituted ammonium functions.

The amine functionality is preferably a secondary amine functionality, including secondary amide functionality and/or a primary ammonium functionality.

When used herein, the term 'bonded' includes both covalent and ion pair bonding. Thus for example moieties bonded via amine functions may be bonded via secondary amine linkages and/or via primary ammonium—acid anion pair bonding.

In one embodiment of this feature of the present invention, we provide a switchable adhesive composition which includes a polymer comprising a backbone polymeric moiety and a plurality of bound-in curable moieties, characterised in that at least a proportion of the bound-in curable moieties comprise free radically active groups having an amine functionality derived from a primary amine.

The switchable polymer may have adhesive properties, in which case it may form the sole adhesive constituent of the adhesive composition, or it may be blended with other adhesives.

The switchable polymer need not itself have adhesive properties, in which case it is blended with one or more adhesives to form a switchable adhesive composition of the invention.

Thus in another embodiment of this feature of the present invention we provide a switchable adhesive composition of the present invention characterised in that it comprises a switchable polymer as hereinbefore described in admixture with a non-switchable adhesive.

For the sake of brevity, whether or not such polymers have adhesive properties they will herein after be referred as "switchable polymer(s)".

It a second aspect therefore the present invention provides a switchable polymer capable of being influenced by radiation to change from one state to another, comprising a backbone polymeric moiety having a plurality of curable moieties bonded thereto, characterised in that at least a proportion of the curable moieties each comprises a free-radically active group and has an amine functionality.

The curable moieties are preferably photocurable moieties. By this term we mean moieties that are capable of undergoing a reaction induced by electromagnetic, in particular by actinic, radiation. Often such moieties will require the presence of a free radical initiator to initiate the reaction under the influence of incident radiation. Such initiators are described further below.

Examples of such reactions include, for example, photo-curing to increase the molecular weight of the polymer to which the moieties are bound.

The preferred curable moieties are those which change the adhesive composition from a tacky to a less tacky, or even non-tacky, state (that is, render it switchable) by producing a polymer of increased molecular weight by way of linking or cross-linking the switchable polymer ('curing').

The curable moieties may be introduced onto the backbone polymeric moiety by forming a polymer comprising the backbone polymeric moiety and chemically bonding a precursor of the curable moiety to the backbone polymeric moiety.

The switchable adhesive composition of the present invention preferably has a peel strength in its non-tacky state that is at most 50% of that in its tacky state, preferably at most 25 or 20%, in particular 10%.

Any conventionally known adhesive polymers may be used to form the backbone polymeric moiety provided that such polymers are, where desirable, reactable to bond the curable moieties onto them.

This may occur, for example, by forming covalent and/or ion pair adducts or condensates with the precursors of the curable moieties.

Preferred backbone polymeric moieties include polyurethanes, polyacrylics and free radical polymerisable vinyl moieties. Polyacrylics are especially preferred.

Particularly preferred materials forming the backbone polymeric moiety are acrylic adhesives.

By the term acrylic adhesives we include adhesives based on polymers of acrylates, methacrylates, other derivatives of acrylic and methacrylic acids, and copolymers of the same.

Indeed acrylic copolymer adhesives are especially preferred, for example alkyl acrylate based copolymers.

The backbone polymeric moiety may be a copolymer of one or more acrylic species. It may be a copolymer of one or more acrylics and a free radically polymerisable vinylic compound.

Such vinylic compounds include preferred compounds that also comprise functions other than vinylic olefin, such as carboxylic acid derivatives, for example anhydrides, in particular cyclic anhydrides, such as itaconic anhydride and maleic anhydride; ester derivatives, in particular lactones, such as vinyl azlactone; and hydroxyesters, such as glycidyl methacrylate; preferably cyclic anhydrides, and in particular itaconic anhydride.

Apt acrylic adhesives include those wherein the backbone polymeric moiety includes a proportion of unreacted residues that are capable of being derivatised by a precursor of the curable moiety, such as carboxylic acid residues, for example acrylic or methacrylic acid residues.

These may be for example esterified with hydroxyl groups, or reacted with primary amine groups, in a precursor of the curable moiety. Bonding of the curable moiety to the backbone acrylic moiety is preferably effected via an amide linkage and/or via a substituted ammonium—carboxyl anion pair bond.

Unreacted acid derivative residues on the backbone that are more reactive than carboxylic acid residues are particularly advantageous since they may be derivatised more readily.

Examples include moieties that are residues in the backbone polymeric moiety of the types of vinylic compounds mentioned above, for example itaconic anhydride, which may be similarly esterified, amidated, etc.

Bonding of the curable moiety to the backbone acrylic moiety is again preferably effected via an amide linkage and/or via a substituted ammonium—carboxyl anion pair bond.

Especially apt acrylate copolymers are acrylate terpolymers where the backbone polymeric moiety is an alkyl acrylate/alkyl acrylate/acrylic acid terpolymer.

Suitably, the backbone polymeric moiety is an n-butyl acrylate/2-ethylhexyl acrylate copolymer.

Examples of such include n-butyl acrylate/2-ethylhexyl acrylate/acrylic acid in the ratio 47/47/6. Such an adhesive composition is often referred to as A8 adhesive.

Especially preferred acrylic copolymers are those copolymers that also incorporate a functional monomer that is a free radically polymerisable vinylic compound as described supra. The most preferred acrylic copolymers are those in which the free radically polymerisable vinylic compound is derived from itaconic anhydride.

Suitable polyurethanes for use as the switchable polymer in the adhesive composition can be derived from a polyester diol or preferably a polyether diol and a di-isocyanate. Suitable polyether diols include polyoxyalkylene diols in which the alkylene contains 2 to 4 carbon atoms such as polyoxyethylene, polyoxypropylene and polyoxytetramethylene diols and mixtures thereof.

Such polyether diols can suitably have an average molecular weight of 1000 to 8000 and preferably have a molecular weight of 1500 to 6000. A favoured polyether diol for forming the polyurethanes used in the invention is polyoxypropylene diol. An apt diol of this type is known as PPG 2025, available from British Drug House, which has an average molecular weight of 2025.

Another suitable diol, which contains hydrophilic groups, is a block copolymer of polypropylene glycol and ethylene oxide marketed as Dowfax 63N10 (Trade Mark) available from Dow Chemicals Inc.

Polyoxyalkylene diol residues can be used to render the adhesive formed therefrom moisture vapour transmitting.

Diisocyanates used to form the polyurethane may suitably have an isocyanate functionality of 1.6 to 2.05. They preferably have an isocyanate functionality of about 2.0.

Suitable diisocyanates include an aliphatic (including alicyclic) and aromatic diisocyanates.

Favoured diisocyanates include toluene diisocyanate, 4,4'-diphenylmethane diisocyanate and 4,4'-dicyclo hexyl methyl diisocyanate.

The latter is the preferred diisocyanate, which in an apt form is known as Desmodur W (Trade Mark) available from Bayer.

The polyurethane can optionally include a chain extending agent. Suitable chain extending agents include diols such as ethane diol and butane diol, diamines for example ethylene diamine, and water.

The molar ratio of diol or diol and diamine residues to diisocyanate residues in the polyurethane can suitably be 0.6 to 0.8:1 and preferably 0.65 to 0.75:1 for example 0.7:1.

This leaves free isocyanate residues on the backbone polymeric moiety, which are capable of further reaction inter alia with the amine function of the precursor of the curable moiety to link the latter to the backbone polymeric moiety by a ureido linkage.

The proportion of the precursor compound that possesses a free radically active vinyl group and which has primary amine functionality is desirably such as to react with from 15 to 25% of the free isocyanate groups in the polyurethane.

The remainder of the free isocyanate groups may react with, for example, hydroxyl group containing compounds, which are present as chain terminators.

Mono-ols that are tackifying agents can be used to react with free isocyanate groups of the polyurethane. Such mono-alcohols include hydrogenated mono hydroxy tackifying resins, for example hydrogenated abietyl alcohol.

A hydrophilic polyurethane can be formed by suitable choice of polyether diol.

Such a polyurethane may be hydrated, and when hydrated may contain from 35 to 95% by weight of water, aptly 50 to 92%, preferably 70 to 90% and more preferably 75 to 85% by weight. The degree of water absorption can be determined by taking a known weight of the polyurethane and immersing in water for 24 hours.

The hydrated polymer is removed from the water, excess water is removed by lightly blotting with absorbent paper and then the hydrated polyurethane is weighed.

The water absorption of the polyurethane (percentage by weight) can then be calculated as (weight of hydrated polyurethane-weight of dry polyurethane)×100/weight of hydrated polyurethane.

When the backbone polymeric moiety comprises a polyurethane adhesive it may be a lightly cross-linked or linear polyurethane adhesive.

When the backbone polymeric moiety is a polyurethane the curable groups may form end groups on the polyurethane backbone, may be incorporated into the polymer backbone or may be pendent groups, for example along the backbone.

Suitable precursors of the curable moieties include any compounds that comprise a free-radically active vinylic group and have an amine functionality that is able to react with functional groups on the backbone polymeric moiety.

Preferred precursors include alkenylarylamines, in particular $C_{1-6}$ alkenyl-$C_{6-10}$ aryl-amines, such as p-vinylaniline; 1- or 2-amino-$C_{1-6}$ alk-1-en-1-yl-$C_{1-6}$ alkanoates, such as aminovinyl acetate; 1- or 2-amino-1-halo-$C_{1-6}$ alk-1-enes, such as aminovinyl chloride; 1- or 2-amino-1-cyano-$C_{1-6}$ alk-1-enes, such as aminoacrylonitrile; 1- or 2-amino-$C_{1-6}$ alk-1-enoic acids and $C_{1-6}$ alkyl esters thereof, such as amino(meth)acrylic acid and methyl amino(meth)acrylate; and vinylamine. Especially preferred is p-vinylaniline.

The amount of the curable moiety present in the switchable adhesive composition may vary, depending, inter alia, upon the amount of tackiness desired in the switchable adhesive when it is switched from its tacky to its less or non-tacky state.

Thus, the amount of the curable moiety present in the switchable adhesive composition may be from 0.4 to 50% by weight of backbone polymeric moiety preferably from 0.4 to 40% by weight and more preferably from 0.4 to 20% by weight.

The switchable adhesive compositions of the invention will often be include or be used in conjunction with a free radical initiator that reacts to electromagnetic radiation. Any conventionally known free radical photoinitiators may be used. Particularly preferred are those which react to visible light radiation, although initiators that react under longer or shorter wavelength light may be used in compositions of the invention.

Thus, free radical initiators that may be mentioned include titanocene photoinitiators; dye-and-co-initiator systems, for example thionine and triethanolamine; dye-and-borate salt systems; dye-and-peroxide systems and 1,2-diketone/co-initiator systems, for example camphorquinone and tertiary amine.

Preferred free radical initiators include titanocene initiators such as bis(hapto⁵-cyclopentadienyl)bis[2,6-difluoro-3-(IH-pyrr-l-yl)phenyl]-titanium, sold as Irgacure 784 (Trade Mark) in the UK by Ciba Geigy.

Initiators that react with UV light may be used, such initiators include the Irgacures, such as Irgacure 651 (benzyl dimethyl ketal) or Irgacures 907 (2-methyl-1-[4-(methylthio)phenyl]-2-morpholino-propan-1-one); or the Uvatones, such as Uvatone 8302 (2,2-diethoxy-1,2-diphenyl ethanone).

The switchable adhesives of the invention are preferably provided with a photoinitiator.

According to a third feature of the invention we provide a process for the manufacture of an adhesive composition as hereinbefore described characterised by admixing a switchable adhesive of the present invention with other conventional components of adhesive compositions, and optionally with at least one adhesive.

In one embodiment of this feature of the present invention, we provide a process for the manufacture of an adhesive composition as hereinbefore described, characterised by reacting a) a backbone polymer as hereinbefore described with b) a precursor of a curable moiety as hereinbefore defined.

In another embodiment of this feature of the present invention, in particular we provide a process for the manufacture of an acrylate switchable adhesive composition as hereinbefore described, characterised by reacting a) an acrylate backbone polymer containing unreacted carboxylic acid groups and the residue of a free radically active vinyl moiety with b) a curable compound that possesses a free-radically active vinyl group and has a primary amine functionality to produce an adhesive composition comprising a backbone polymeric moiety with bound-in curable groups.

In a fourth feature of the invention we provide a process for manufacturing a switchable polymer of the invention, characterised by reacting a) a backbone polymer comprising a backbone polymer as hereinbefore described with b) a precursor of a curable moiety comprising a free-radically active group and a primary amine functionality.

In particular, we provide a process for the manufacture of an acrylic switchable adhesive polymer as hereinbefore described characterised by reacting a) an acrylic backbone polymer containing unreacted carboxylic acid groups and optionally a cyclic anhydride group, a cyclic amide group, or a hydroxyester, with b) a curable compound that possesses a free-radically active vinylic group and has a primary amine functionality.

The curable groups may be end groups, pendant groups or may be incorporated into the backbone.

We also provide a process for the manufacture of a polyurethane switchable polymer as hereinbefore described, characterised by reacting a polyurethane that comprises free isocyanate groups with a free radical curable moiety possessing a free-radically active vinyl group and having a primary amine functionality.

As noted above, preferred curable moieties include photocurable moieties.

Preferred curable moieties also include those which change the adhesive composition from a tacky to a less or non-tacky state by producing a polymer of increased molecular weight by way of linking or cross-linking the switchable polymer. Such curing may be initiated by visible light or longer or shorter wavelength light such as infra red or ultra violet light.

Whilst it is preferable that the curable moiety reacts via a free radical reaction, it is most desirable that the reaction of the curable groups is visible light initiated. Thus the wavelength of the light used may be less than 700 nm, for example preferably between 400 and 700 nm.

The dosage of light used may vary depending upon the switchable adhesive composition but is generally greater than 0.4 mW cm$^{-2}$ when UV light is used.

When a visible light switchable adhesive composition is used, ambient light may be used and therefore the dosage may vary.

As noted above, the switchable polymers of the invention may also be blended with a conventional adhesive composition to produce an adhesive mixture that is switchable.

The adhesives of the invention are preferably pressure sensitive adhesives (PSAs) and are particularly advantageous in the manufacture of adhesive tapes and adhesive dressings. By the term dressings we include wound dressings, adhesive bandages and adhesive tapes for medical use.

The adhesives may also be useful in the manufacture of other conventional products that require a peelable adhesive, e.g. masking tapes, stencils, etc.

Thus according to the invention we provide the use of a composition as hereinbefore described in the manufacture of an adhesive dressing.

Dressings comprising adhesive compositions of the invention are also themselves novel.

Thus according to a further feature of the invention we provide an adhesive product comprising a backing layer substantially coated on at least one surface thereof with an adhesive composition as hereinbefore described.

In one embodiment of this feature of the present invention, we provide an adhesive dressing comprising a backing layer substantially coated on at least one surface thereof with an adhesive composition as hereinbefore described.

It will be appreciated that the switchable adhesive composition of the present invention will tend to begin to change from a tacky to a less tacky state once its curing reaction has been initiated by any radiation to which it is susceptible. Thus, for storage stability the adhesive product should be in a form that prevents initiation of the curing reaction.

Accordingly, where exposure to the relevant radiation is sufficient to initiate the reaction, with or without a photoinitiator in the adhesive composition, the adhesive composition in the adhesive product should be shielded from the radiation by means of sufficient occlusive materials. (By 'occlusive' we mean that the material is occlusive over the wavelength range in which the adhesive composition is switchable and/or in which the photoinitiator absorbs.)

Particularly preferred adhesive compositions of the present invention are those which react to visible light radiation. Accordingly, it is particularly preferred that any occlusive components are occlusive to visible light radiation. Thus, for example, the product may be stored in an occlusive pouch, it may be provided with an occlusive backing layer if for example in the form of a roll, and with one or more occlusive release liners on the adhesive composition if not.

All such products, but in particular those which are visible light sensitive, should be adapted to permit the adhesive to be irradiated as and when appropriate to permit ready removal of the product from any substrate to which it has been applied.

In such cases, the backing layer preferably comprises a removable occlusive layer overlying a transmissive, that is, transparent or translucent, layer that bears the adhesive composition on a face away from the occlusive layer. We especially prefer an occlusive layer that is visible light occlusive, and a transmissive layer that is visible light transmissive.

It is preferred that the occlusive layer is continuous; however, the transmissive layer may be a continuous layer, or any variety of discontinuous layer. The latter includes perforated layers, and integral net layers where the area of the voids in the net exceeds the area of the material of the layer. It also includes all structures intermediate in structure between those mentioned here.

The adhesive coating may be a continuous coating or non-continuous coating, e.g. may be a pattern spread adhesive on a continuous surface of the backing layer. Where the backing layer comprises a transmissive layer, the adhesive will form a coating on the transmissive layer, which coating may again be continuous or non-continuous.

The occlusive layer should of course fully overlie the adhesive composition.

The occlusive and transmissive layers may be reversibly bonded together in any manner.

For example, the occlusive layer may be adhesively bonded to the tranmissive layer. If adhesively bonded, then the peel strength of the bonding adhesive must be less than that of the switchable adhesive composition in its tacky form.

In use, an adhesive product, in particular a dressing, of the invention may be applied to the skin of a patient.

When it is desired to remove or replace the product, the occlusive layer may be removed. The adhesive on the substrate-facing, in particular skin-facing, surface of the transmissive layer can then be exposed to a source of appropriate electromagnetic radiation, preferably visible.

After a given time the peel strength of the adhesive will be reduced allowing the transparent layer to be removed from the substrate, in particular the patient's skin.

Thus according to the invention we provide an adhesive product, in particular a dressing, as hereinbefore described comprising a backing layer and an adhesive layer, characterised in that a) the backing layer comprises a removable occlusive layer and a transmissive layer between the occlusive layer and the adhesive layer and b) the adhesive layer comprises a switchable adhesive composition as hereinbefore described.

Any conventionally known occlusive and transmissive materials may be used in the backing layer of the adhesive product, in particular the dressings, of the invention. Preferred adhesive products, in particular dressings are those which comprise a film, for example a thin film, backing layer, that is, both the occlusive and transmissive layers comprise or are a film.

However, other backing layers, for example fabric layers, may also be considered appropriate.

The adhesive products, in particular the dressings, of the invention may be manufactured using conventional methods known per se.

According to a further feature of the invention we provide a method of use of the adhesive product of the present invention, characterised by adhesively contacting a part of the adhesive product bearing an adhesive composition of the invention to a substrate.

The method may also include the removal of a such a product which comprises an occlusive layer and a transmissive layer by a) removing the occlusive layer from the product and then b) irradiating the adhesive composition through the transmissive layer to render the adhesive composition less tacky.

The dressings of the invention are especially useful in the treatment of wounds.

Thus according to a further feature of the invention we provide a method of treating a wound on a patient, characterised by adhesively applying a dressing of the invention to the wound.

The method may also include the removal of such a dressing which comprises an occlusive layer and a transmissive layer by a) removing the separated layer from the product and then b) Irradiating the adhesive composition through the transmissive layer to render the adhesive composition less tacky.

According to a further feature of the invention we provide a method of use of the adhesive product system of the present invention as hereinbefore defined, characterised by adhesively contacting a part of the adhesive product bearing an adhesive composition of the invention to a substrate, and on or after such adhesive contact bringing the adhesive composition and the photoinitiator into intimate contact.

The method may also include the removal of such a product which comprises an occlusive layer and a transmissive layer by a) removing the occlusive layer from the product and then b) irradiating the adhesive composition through the transmissive layer to render the adhesive composition less tacky.

The dressing systems of the invention are especially useful in the treatment of wounds.

Thus according to a further feature of the invention we provide a method of treating a wound on a patient, characterised by adhesively applying a dressing system of the invention to the wound and on or after such application bringing the adhesive composition and the photoinitiator into intimate contact.

The method may also include the removal of a dressing which comprises an occlusive layer and a transmissive layer by a) removing the separated layer from the product and then b) irradiating the adhesive through the transmissive layer to render the adhesive composition less tacky.

Many medicinal agents are suitable for incorporation into the adhesive compositions of the present invention.

By medicinal agent is meant pharmacologically active agents including agents that are topical anaesthetics such as xylocaine, bacteriostatic agents such as silver nitrate; antibacterial agents of which preferred forms are silver sulphadiazine and chlorhexidine salts; and antibiotics; topical steroids, enzymes; tissue stimulants; coagulants and anticoagulants and antifungal agents.

Other agents such as emollients may also be added.

The invention will now be illustrated with reference to the accompanying drawings and Examples.

BRIEF DESCRIPTION OF DRAWINGS

With reference to FIG. 1, a dressing (1) comprises a backing layer (2) and an adhesive layer (3) of a switchable pressure-sensitive adhesive (PSA) of the present invention that has pendant acrylate groups.

Figure 1:
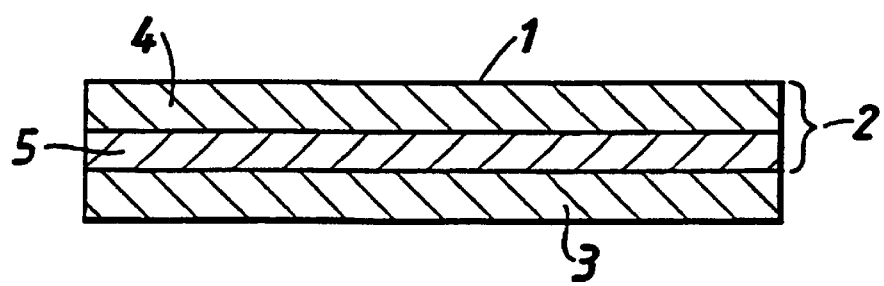
FIG. 1 is a cross-section of a dressing of the invention.

The backing layer (2) comprises an occlusive layer (4) and a transmissive layer (5) between the occlusive layer (4) and the adhesive layer (3). The dressing may optionally be provided with appropriate carrier layers and protector layers.

In use the dressing (1) is adhered to the skin of a patient when the adhesive layer (3) is in a tacky form.

When it is desired to remove the dressing (1) from the patient, the occlusive layer (4) is removed exposing the transparent layer (5) and thereby the adhesive layer (3) to visible light.

The visible light causes the photoinitiator to initiate the free-radical cross-linking of the PSA through the pendant acrylate groups resulting in the adhesive losing its tackiness and peel strength. The time required for this reaction to be complete may vary, for example, from 1 to 15 minutes. The dressing may then be removed with reduced trauma to the patient.

Figure 2:
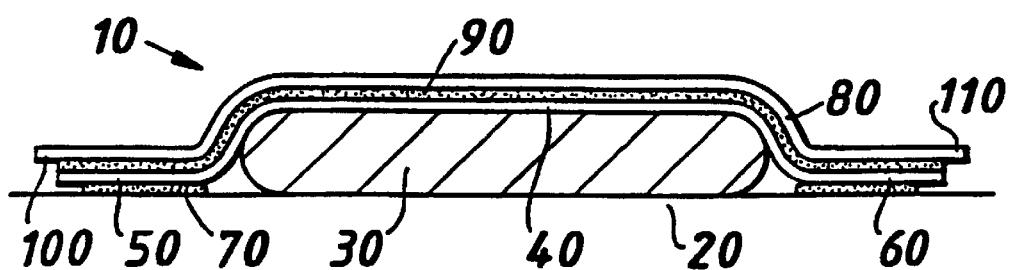
FIG. 2 is a cross-section of a further dressing embodiment of the invention when in use on a patient.

Referring now to FIG. 2, a medical dressing (10) is shown attached to a patient's skin (20).

The dressing (10) comprises a wound facing absorbent layer (30) which is underneath a protective backing layer (40).

At opposed edges (50, 60) the backing layer (40) is provided with adhesive layer (70) that comprises a switchable polymer having groups that can be cross-linked under the influence of UV or visible light.

The backing layer (40) is provided with a cover (80) which is releasably secured to the backing layer (40) by a weak adhesive (90). Alternatively the cover (80) may be laminated to the backing layer (40). For ease of removal the cover (80) overlaps the backing layer (40) at its edges (100, 110).

When it is desired to remove the dressing from the skin of a patient, the cover (80) can be gripped at its edges (100, 110) and peeled off the backing layer (40). This exposes the adhesive layer (70) to UV or visible light irradiation.

This irradiation acts so as to cure the switchable polymer in the adhesive layer. This, after a certain time (depending upon the adhesive used), causes the adhesive layer (70) to lose its tackiness to such an extent so that the dressing can be removed without causing trauma to the patient.

The removal of the cover (80) should not itself cause removal of the dressing before switching. Accordingly, the peel strength of the adhesive (90) adhering the cover (80) to the backing layer (40) should be substantially less than that of the adhesive layer (70) adhering the dressing (10) to the patient's skin.

The adhesive (70) loses tackiness on exposure to UV or visible light. It is therefore desirable that the adhesive layer (70) is not exposed to the light for a substantial period when the dressing (10) is applied to a patient. Thus the adhesive layer (70) may be initially provided on the surface with release paper (not shown) which is opaque to UV and visible light and which can be readily removed from the adhesive so that the dressing is ready for use.

The preparation and testing of adhesives suitable for use as the adhesive layer (70) will now be described in the following Example.

(a) Preparation of 'Backbone Polymer'

111 g of ethyl acetate (solvent) was refluxed under a nitrogen gas purge in a 750 ml flask for 20 minutes at 70° C. Thereafter a solution of 0.0178 g of bis(4-t-butylcyclohexyl)peroxy dicarbonate (BCHPC) in 5 ml ethyl acetate was added to the contents in the flask. The monomers, 47 g of ethylhexylacrlate, 47 g of n-butyl acrylate, 2 g of acrylic acid and 4 g of itaconic anhydride were gradually added in 10 ml aliquots to the flask over a period of 1.5 hours.

The reaction mixture was diluted with a further 30 ml of solvent and stirred for a further 1.5 hours after which a solution of 0.448 g of BCHPC in 40 ml of solvent was added in 10 ml aliquots every 30 minutes.

The reaction solution was further diluted with 126 g of solvent after the final BCHPC addition and left to react for a further 9 hours.

(b) Functionalising the "Backbone Polymer"

1. To 92.06 g of the 'backbone' polymer solution was added 1.38 g of vinyl aniline and the reaction mixture, maintained at room temperature, was stirred for 3.5 hours to yield a switchable adhesive composition of the invention, designated as the 'invention adhesive'. The reaction was monitored using infra-red spectroscopy by following the loss of the anhydride at 1849 and 1774 cm$^{-1}$.

2. To 106.64 g of the backbone polymer solution, was added 1.38 g of hydroxyethyl methacrylate and about 5% by weight (based on the weight of HEMA) of sulphuric acid catalyst. The reaction mixture was heated to a temperature of 50° C. under a blanket of compressed air. It was maintained at that temperature, with stirring for about 20 hours to complete the reaction and form a switchable adhesive designated as the 'control adhesive'. The reaction was monitored using infra-red spectroscopy by following the loss of the anhydride at 1849 and 1774 cm$^{-1}$.

(c) Testing

Both the invention and the control adhesives were tested by spreading each adhesive solution onto a polyethylene terephthalate film (sold under the Trade Mark MELINEX) to a thickness of 0,25 mm and leaving the coated film to dry overnight, at room temperature and in the dark.

25 mm wide strips of both invention and control adhesive coated films were applied to plates fabricated from high density polyethylene (HDPE) whilst being kept under darkened conditions for a period of 20 minutes at 23° C. at 50% relative humidity.

Half the film coated film plates were then exposed to visible light radiation from a lamp for a period of 10 minutes.

The coated films were then peeled from the HDPE plates at a rate of 300 mm min$^{-1}$ in accordance with a 180° peel test as described in the British Pharmacopoeia, Appendix XXII (Test 2). The test results are given in the following table.

| Sample | Peel Strength (N/m) | |
| --- | --- | --- |
| | Unexposed Coated Film | Exposed Coated Film |
| Invention | 500 (Steady Peel) | 24 (adhesive failure) |
| Control | 360–416 (cohesive failure) | 24 (adhesive failure) |

The results clearly demonstrate that the novel adhesive compositions of the invention perform at least as well as the control example but can be made by a far simpler method.

A further test was carried out on an invention adhesive coated tape as described above except that the tape was exposed to light for only 5 minutes.

The peeling force under these conditions was 36 N/m resulting in adhesive failure.

What is claimed is:

1. A switchable adhesive composition capable of being influenced by radiation to change from a tacky to a less tacky state which includes a switchable polymer capable of being influenced by radiation to change from one state to another, said switchable polymer comprising a backbone polymeric moiety having a plurality of curable moieties bonded thereto, wherein at least a proportion of the curable moieties each comprises a free-radically active group, said polymer being manufactured by reacting:
   a) an acrylic backbone polymer containing unreacted carboxylic acid groups and optionally a cyclic anhydride group, a cyclic amide group, or a hydroxyester, with
   b) a curable compound that possesses a free-radically active vinylic group and has a primary amine functionality.

2. A composition according to claim 1, wherein the curable moieties render it switchable by way of linking or cross-linking the switchable polymer, and it is switchable when exposed to visible light, and optionally includes a free radical photoinitiator which reacts to visible light radiation, chosen from titanocene photoinitiators; dye-and-co-initiator systems; dye-and-borate salt systems; dye-and-peroxide systems and 1,2-diketone/co-initiator systems.

3. A composition according to claim 2, characterised in that the backbone polymeric moiety is a copolymer of n-butyl acrylate and 2-ethylhexyl acrylate, optionally with a free radically polymerisable vinylic compound chosen from cyclic carboxylic acid anhydrides, lactones and hydroxyesters, and the curable moieties comprise a free-radically, active vinylic group and have an amine functionality which has reacted with functional groups on the polymeric backbone moiety, and are present as from 0.4 to 20% by weight of backbone polymeric moiety.

4. A process for manufacturing a switchable polymer as defined in claim 1, comprising reacting
   a) a backbone polymer comprising an acrylic backbone polymer containing unreacted carboxylic acid groups and optionally a cyclic anhydride group, a cyclic amide group, or a hydroxyester with
   b) a precursor of a curable moiety comprising a free-radically active vinylic group and has a primary amine functionality.

5. A process for the manufacture of an adhesive composition according to claim 1, characterised by admixing a switchable adhesive of the present invention with other conventional components of adhesive compositions, and optionally with at least one adhesive.

6. An adhesive product comprising a backing layer substantially coated on at least one surface thereof with an adhesive composition according to claim 1.

7. An adhesive dressing comprising a backing layer substantially coated on at least one surface thereof with an adhesive composition according to claim 1, characterised in that the adhesive composition reacts to visible light radiation, and is shielded from light by a layer occlusive to visible light radiation which fully overlies the adhesive composition.

8. An adhesive dressing according to claim 7, comprising a backing layer and an adhesive layer, characterised in that
   a) the backing layer comprises a removable occlusive layer and a transmissive layer between the occlusive layer and the adhesive layer and
   b) the adhesive layer comprises a switchable adhesive composition as hereinbefore described.

9. A method of use of an adhesive product according to claim 8, comprising adhesively contacting a part of the adhesive product bearing an adhesive composition of the invention to a substrate, characterised by subsequently
   a) removing the occlusive layer from the product and then
   b) irradiating the adhesive composition through the transmissive layer to render the adhesive composition less tacky.

* * * * *